(12) United States Patent
Seshadri et al.

(10) Patent No.: US 11,324,849 B2
(45) Date of Patent: May 10, 2022

(54) FRAGRANCE DISPENSER WITH USER-SELECTABLE RELEASE RATE

(71) Applicant: 3M INNOVATIVE PROPERTIES COMPANY, St. Paul, MN (US)

(72) Inventors: Kannan Seshadri, Woodbury, MN (US); Brenda K. Balderas, Woodbury, MN (US); Jordan A. Fleischer, Minneapolis, MN (US); Fiona E. Menken, Woodbury, MN (US); Danielle M. Schreppel, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 657 days.

(21) Appl. No.: 16/311,528

(22) PCT Filed: Jun. 27, 2017

(86) PCT No.: PCT/US2017/039400
§ 371 (c)(1),
(2) Date: Dec. 19, 2018

(87) PCT Pub. No.: WO2018/005423
PCT Pub. Date: Jan. 4, 2018

(65) Prior Publication Data
US 2020/0306404 A1 Oct. 1, 2020

Related U.S. Application Data

(60) Provisional application No. 62/356,668, filed on Jun. 30, 2016.

(51) Int. Cl.
*A61L 9/12* (2006.01)
*A61L 9/03* (2006.01)
*A61L 9/04* (2006.01)

(52) U.S. Cl.
CPC ............... *A61L 9/122* (2013.01); *A61L 9/035* (2013.01); *A61L 9/048* (2013.01);
(Continued)

(58) Field of Classification Search
CPC .......... A61L 9/122; A61L 9/035; A61L 9/048; A61L 2209/131; A61L 2209/133; A61L 2209/16; A61L 9/125; A61L 9/046
See application file for complete search history.

(56) References Cited

U.S. PATENT DOCUMENTS 4,095,031 A   6/1978 Engle
4,157,787 A   6/1979 Schwartz
(Continued)

FOREIGN PATENT DOCUMENTS

WO   WO 2002-09776   2/2002
WO   WO 2010-068479  6/2010
(Continued)

OTHER PUBLICATIONS

"Characteristics of An Airfoil", Experiment 6, ME 410, [retrieved from the internet on Jan. 31, 2019], URL <http://www.me.metu.edu.tr/courses/me410/exp6/exp6.html>.
(Continued)

*Primary Examiner* — Sean E Conley
*Assistant Examiner* — Brendan A Hensel
(74) *Attorney, Agent, or Firm* — Kenneth B. Wood (57) ABSTRACT

A fragrance dispenser and a corresponding method of dispensing fragrance, comprising at least one receptacle having a major open end, with a porous diffuser layer occlusively overlying the major open end of the receptacle, wherein at least a sectional area of the porous diffuser layer is removable to uncover a portion of the receptacle to control of the release rate of a fragrance source. The fragrance dispenser may comprise a plurality of receptacles and the porous
(Continued)

diffuser layer comprises a plurality of sections that are individually removable to uncover each receptacle. The fragrance dispenser could comprise a removable cover sheet that is peelably detachable from the porous diffuser layer. Porous diffuser layer could be an organic polymeric nonwoven web and/or the receptacle is made of a thermoplastic organic polymeric resin. The fragrance dispenser may further comprise a secondary diffuser layer that has 50% more permeability that the porous diffuser layer.

19 Claims, 6 Drawing Sheets

(52) U.S. Cl.
CPC ... *A61L 2209/131* (2013.01); *A61L 2209/133* (2013.01); *A61L 2209/16* (2013.01)

(56) References Cited

U.S. PATENT DOCUMENTS

| | | | |
|---|---|---|---|
| 4,874,129 A | 10/1989 | DiSapio | |
| 5,230,867 A | 7/1993 | Kunze | |
| 5,478,505 A | 12/1995 | McElfresh | |
| 5,518,790 A * | 5/1996 | Huber | B32B 27/36 428/35.2 |
| 5,527,493 A | 6/1996 | McElfresh | |
| 5,547,636 A | 8/1996 | Vick | |
| 5,698,166 A | 12/1997 | Vick | |
| 5,861,128 A | 1/1999 | Vick | |
| 6,109,537 A | 8/2000 | Heath | |
| 6,117,218 A | 9/2000 | Snyder | |
| 6,881,776 B2 | 4/2005 | Butuc | |
| 7,754,198 B2 | 7/2010 | Whitehead | |
| 7,833,515 B2 | 11/2010 | Corzani | |
| 8,043,606 B2 | 10/2011 | MacBeath | |
| 8,603,963 B1 | 12/2013 | Steward | |
| D766,416 S | 9/2016 | Seshadri | |
| 2007/0183940 A1* | 8/2007 | Yamamoto | A01M 1/2033 422/124 |
| 2010/0308130 A1 | 12/2010 | Gruenbacher | |
| 2012/0079945 A1 | 4/2012 | Roberts | |
| 2017/0008261 A1* | 1/2017 | Jean-Mary | B32B 7/02 |
| 2020/0297886 A1* | 9/2020 | Uesugi | A61L 9/16 |

FOREIGN PATENT DOCUMENTS

| | | |
|---|---|---|
| WO | WO 2013-014078 | 1/2013 |
| WO | WO 2016-011038 | 1/2016 |

OTHER PUBLICATIONS

Leonardos, "Odor Threshold Determinations of 53 Odorant Chemicals", Journal of the Air Pollution Control Association, 1969, vol. 19, No. 02, pp. 91-95.

International Search Report for PCT International Application No. PCT/US2017/039400, dated Jan. 31, 2018, 4 pages.

* cited by examiner

FRAGRANCE DISPENSER WITH USER-SELECTABLE RELEASE RATE

BACKGROUND

Fragrance dispensers are often used e.g. to enhance the ambience of residences, retail businesses, offices, public areas and so on.

SUMMARY

Herein is disclosed a fragrance dispenser that comprises at least one receptacle having a major open end, with a porous diffuser layer occlusively overlying the major open end of the at least one receptacle. At least a sectional area of the porous diffuser layer is removable. These and other aspects of the invention will be apparent from the detailed description below. In no event, however, should this broad summary be construed to limit the claimable subject matter, whether such subject matter is presented in claims in the application as initially filed or in claims that are amended or otherwise presented in prosecution.

Like reference numbers in the various figures indicate like elements. Some elements may be present in identical or equivalent multiples; in such cases only one or more representative elements may be designated by a reference number but it will be understood that such reference numbers apply to all such identical elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated. Although terms such as "top", bottom", "upper", "lower", "under", "over", "outward", "inward", "up" and "down", and "first" and "second" may be used in this disclosure, it should be understood that those terms are used in their relative sense only unless otherwise noted.

As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties). The term "substantially", unless otherwise specifically defined, means to a high degree of approximation (e.g., within +/−10% for quantifiable properties) but again without requiring absolute precision or a perfect match. Terms such as same, equal, uniform, constant, strictly, and the like, are understood to be within the usual tolerances or measuring error applicable to the particular circumstance rather than requiring absolute precision or a perfect match.

The term "front" is used to denote that major side of a fragrance dispenser that comprises a porous diffuser layer bonded thereto. The term "rear" is used to denote the opposing major side. These terms are used purely for convenience of description and do not denote or necessitate any particular configuration in which the dispenser is to be positioned for use. The term "lateral" as applied to a fragrance dispenser means any direction generally in the major plane of the fragrance dispenser; such directions may often coincide at least generally with a major plane of a diffuser layer that is present in the dispenser.

DETAILED DESCRIPTION

Figure 1:
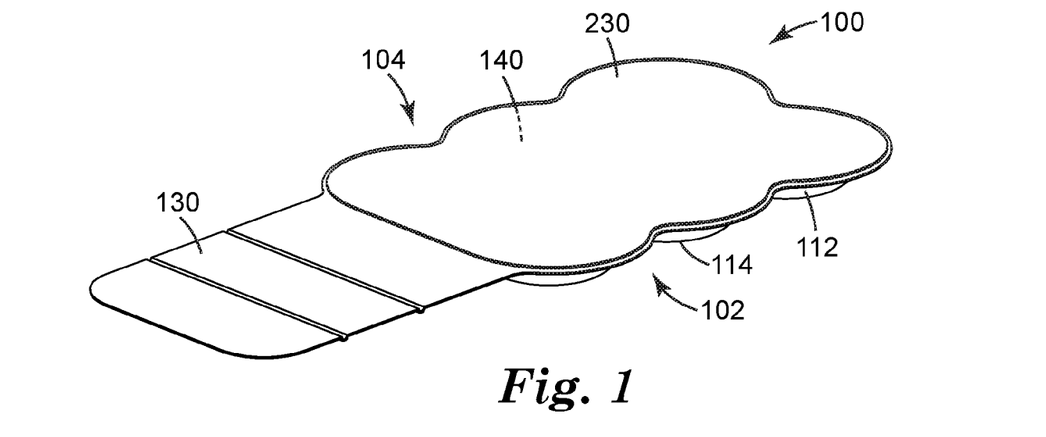
FIG. 1 shows a front/side perspective view of an exemplary fragrance dispenser as disclosed herein.

Shown in FIG. 1 in exemplary embodiment is a fragrance dispenser 100. Dispenser 100 may be at least generally rectangular, or may be elliptical, irregular, etc., in overall shape (as defined e.g. by the lateral perimeter of dispenser 100). Dispenser 100 comprises a base 110 (shown in isolated view in FIG. 2) with a front side 104 and a rear side 102 and comprising at least one receptacle 112 with a major closed end 114 and a major open end 116. In some embodiments, base 110 comprises a plurality of (i.e. at least two) receptacles 112 each with a major closed end 114 and a major open end 116. Dispenser 100 further comprises a porous diffuser layer 140 (visible in the exploded view of FIG. 3) that comprises area(s) 143 (most easily seen in FIG. 5) that occlusively overlie the major open end 116 of the receptacle(s) 112. Each receptacle 112 and a corresponding area 143 of diffuser layer 140 that overlies the receptacle 112 combine to define a receptacle volume of that receptacle. A fragrance source 250 (visible in the exploded view of FIG. 3) is disposed within each receptacle 112. As shown in the exploded view of FIG. 4, in some embodiments a removable cover sheet 230 may be provided atop diffuser layer 140, which cover sheet may be removed by a user of fragrance dispenser 100 when dispenser 100 is to be used.

Base 110 of dispenser 100 may be provided in any suitable manner. In some embodiments, base 110 may be made of a thermoplastic organic polymer. Conveniently, in such embodiments the at least one receptacle 112 may be provided by forming (e.g., molding, e.g. thermoforming or vacuum-forming) the thermoplastic polymer so as to provide at least one thermoformed depression (as viewed from the front side; such a feature will be a protrusion as viewed from the rear side) 128 in the base. In such an arrangement, a rear terminus of a depression 128 can provide the major closed end 114 of a receptacle 112 and a major open end of the depression 128 can provide the major open end 116 of the receptacle. In various embodiments, base 110 may be formed from a sheet comprising a thickness (e.g. before any areas of the sheet are thermoformed) of from about 0.010"

to about 0.40"; in further embodiments, the thickness may be from about 0.025" to about 0.030".

Figure 2:
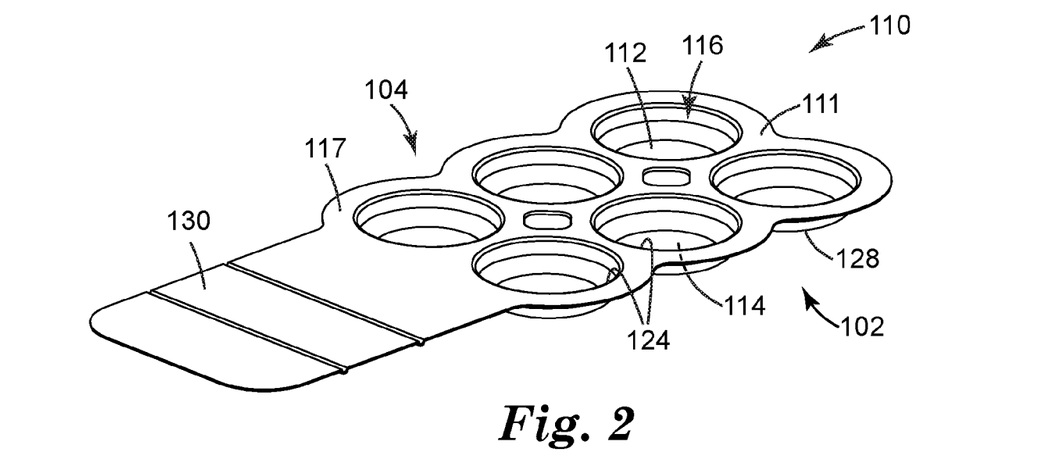
FIG. 2 is an isolated front/side perspective view of an exemplary base of a fragrance dispenser.

In some embodiments, receptacle 112 may take the form of a shallow cavity or basin as illustrated in exemplary embodiment in FIG. 2. Such a shallow cavity may be significantly wider (along at least one lateral dimension that may be at least generally aligned with a major plane of the base) than it is deep (along a dimension at least generally orthogonal to a major plane of the base). In many embodiments, the major open end 116 (which, in use of dispenser 100 after removal of any cover sheet, may be unobstructed e.g. except for the presence of an overlying diffuser layer 140 and optionally an overlying secondary diffuser layer 180 as discussed in detail later herein) may be similar in lateral size and area to the largest lateral size and area of receptacle 112 (such an arrangement is shown in exemplary embodiment in FIG. 2). In other words, in such embodiments major open end 116 is not in the form of a bottleneck or throat. In specific embodiments, the major open end 116 of a receptacle may exhibit an area that is at least about 70, 80, 90, or 95% of the largest area of the receptacle.

Any number of receptacles (e.g. 1, 2, 3, 4, 5, 6, 8, 10 or more) may be used. In some embodiments, some or all of the receptacles may be at least generally coplanar with each other. Receptacles may be arranged in a regular array, or in an irregular pattern, as desired. Receptacles may all be the same shape, or may differ in shape. An individual receptacle may be e.g. circular, square, triangular, rectangular, or irregular in shape. Individual receptacles may all be the same lateral size, or may differ in size. The lateral size of an individual receptacle (as may be established e.g. by the lateral size of a thermoformed depression in a base, as discussed below) may be e.g. at least about 4, 10, 15, or 20 mm. Such a lateral size may be at most about 40, 35, 30, 25, or 25 mm. (The diameter of a generally circular receptacle, or the equivalent diameter of a noncircular receptacle, may be used as the lateral size of the receptacle.) An individual receptacle may have a depth (from the major closed end 114 to the major open end 116) of at least about 1, 2, 3, 4 or 5 mm. An individual receptacle may have a depth of at most about 20, 15, 12, 10, 8, 6 or 4 mm. The number of receptacles, and/or the depth and lateral size of receptacles, can be chosen to provide the desired total (cumulative) amount of fragrance to be delivered. Likewise, at least some such parameters (in particular the ratio of the lateral size of receptacles to the depth of receptacles) can be chosen (e.g. in combination with the porosity of diffuser layer 140) to tailor the rate at which the fragrance is released.

In some embodiments, base 110 may be at least substantially impermeable to volatilizable fragrance. This property may be provided by the material of base 110, by a material that provides a layer of base 110, or by several layers of base 110 in combination. By substantially impermeable is meant that the ratio of the rate at which volatilizable fragrance can leave a receptacle by passing through the material of the base, to the rate at which the volatilizable fragrance can leave the receptacle by passing through the diffuser layer, is less than 0.001 (at 21° C.).

As noted, a porous diffuser layer 140 is positioned (e.g., is attached to the front side 104 of base 110) so that at least one area 143 of diffuser layer 140 occlusively overlies a major open end 116 of at least one receptacle 112. In some embodiments, at least two areas 143 of diffuser layer 140 respectively occlusively overlie the major open ends 116 of at least two selected receptacles 112. In this context, to occlusively overlie means that substantially the only way that volatilizable fragrance can exit a receptacle 112 is by passing as a vapor through (the air-filled passages of) the overlying area 143 of diffuser layer 140. In some embodiments, this may be achieved by bonding (by any suitable means, e.g. via adhesive, heat-sealing, ultrasonic welding, or the like) diffuser layer 140 to one or more bonding areas 117 that partially or completely laterally surround the lateral edges 124 of receptacle(s) 112. (However, as discussed later herein, it may not be necessary that a hermetic seal of each individual receptacle 112 is achieved.)

Diffuser layer 140 is porous, defined herein as meaning that the layer comprises air-filled passageways (e.g., microperforations, interstitial spaces between fibers, interconnected air-filled cells of an open-celled foam, and the like) that extend completely through the diffuser layer from one major surface to another. (It is not necessary, however, that the passageways extend through the layer in a straight line, or along the shortest distance between the major surfaces.) Such air-filled passages allow the passage of volatilized molecules therethrough in vapor form. Porous diffuser layer 140 will be distinguished from a layer that does not comprise porosity (i.e., a layer in which a small molecule, in order to pass through the layer, must solubilize in the solid material of the layer and then move therethrough by molecular diffusion through the solid material, rather than passing through air-filled passageways).

In at least some embodiments, diffuser layer 140 may be at least substantially impermeable to liquids along any dimension thereof. Such a diffuser layer 140, while allowing fragrance molecules in vapor form to pass therethrough so as to exit receptacle(s) 112, may not allow any flow of liquid fragrance (or the liquid form of any other material present in fragrance source 250) e.g. through the thickness of diffuser layer 140 so as to permit the material to escape receptacles 112 in liquid form. In particular embodiments, diffuser layer 140 may not allow any liquid to flow (e.g., by wicking due to capillary action) along the major plane of diffuser layer 140. A porous diffuser layer 140 of this type will be distinguished from e.g. wicking layers and the like that are often used e.g. to facilitate the movement of a liquid through the wicking layer to a location in which the liquid can be evaporated and/or to spread the liquid over a wider area so that is can be more rapidly evaporated.

Figure 3:
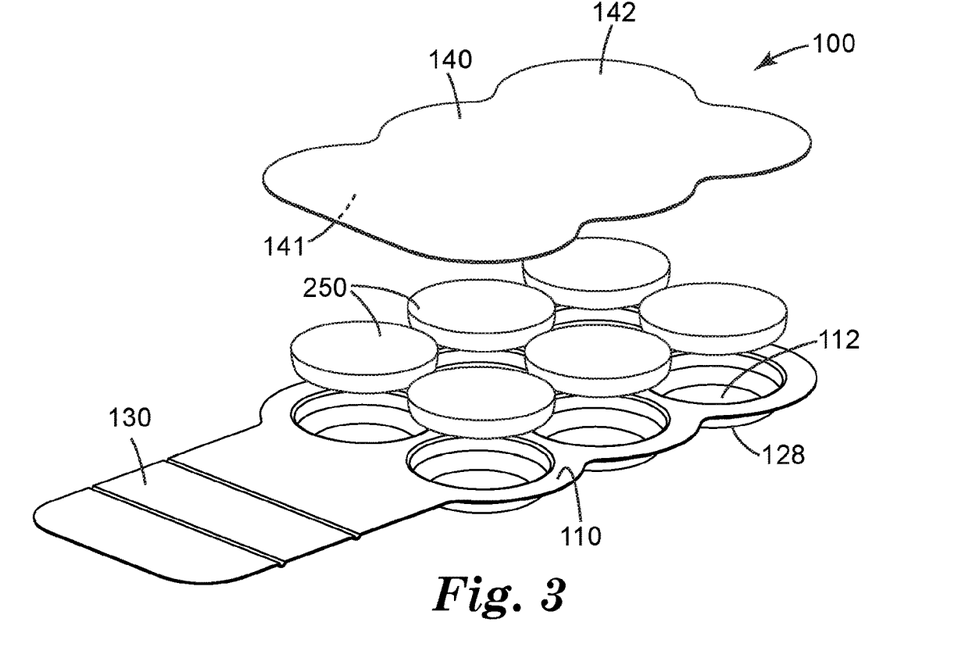
FIG. 3 is a front/side perspective exploded view of an exemplary fragrance dispenser, with a removable cover sheet omitted.
Figure 4:
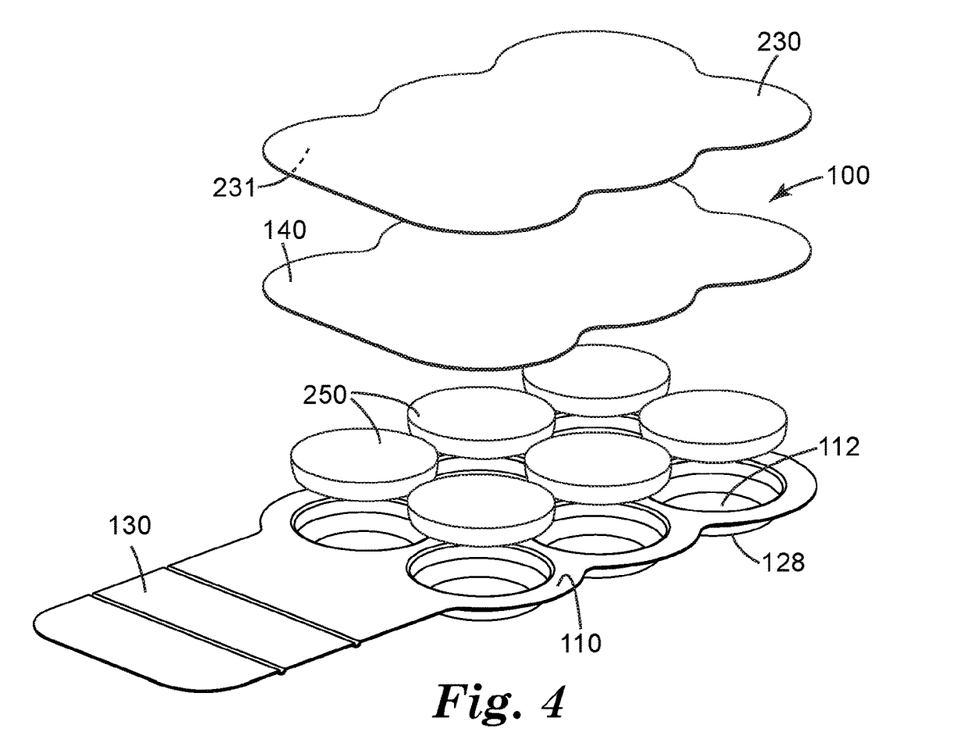
FIG. 4 is a front/side perspective exploded view of an exemplary fragrance dispenser.
Figure 5:
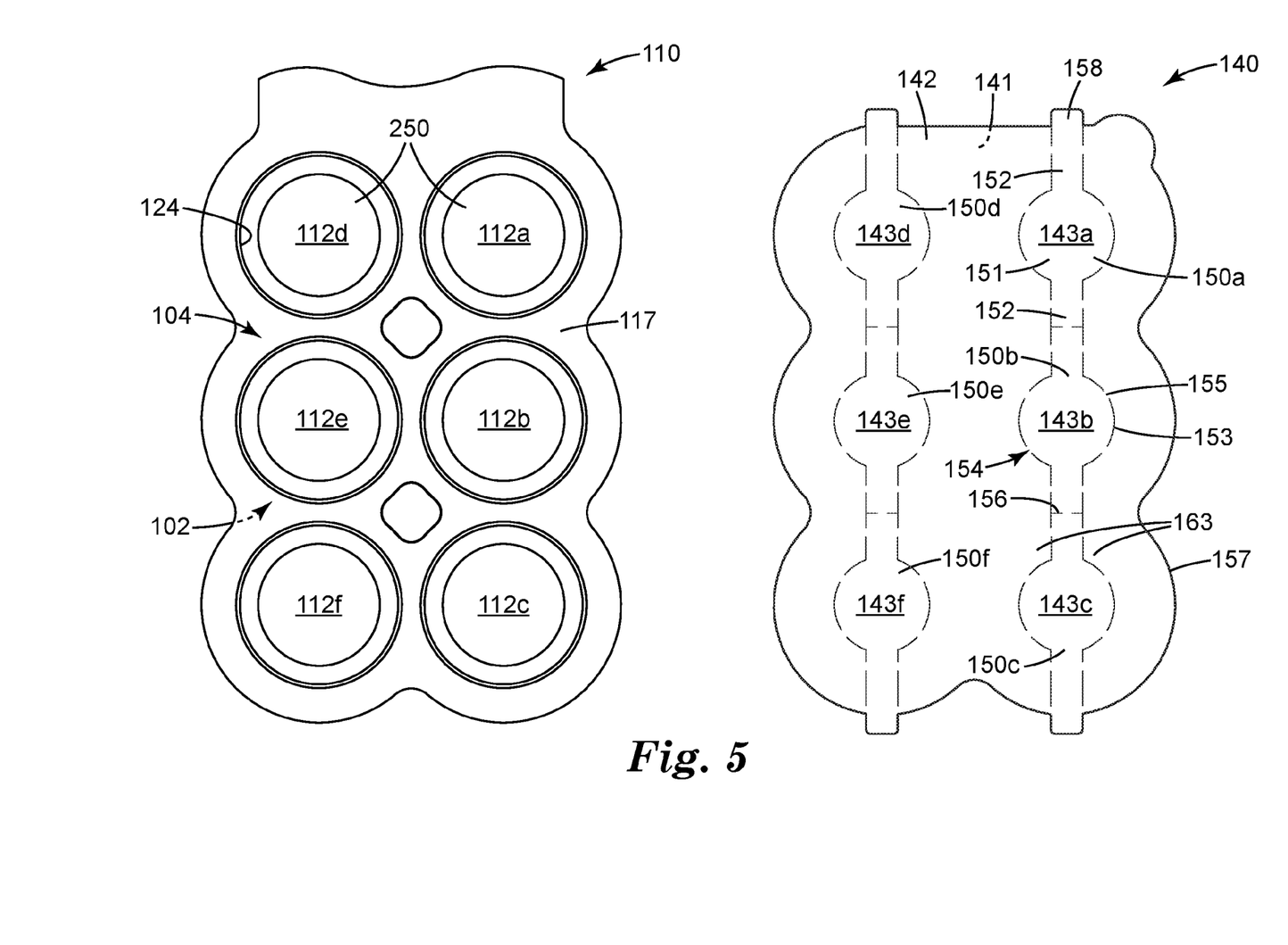
FIG. 5 is a front plan view of another exemplary fragrance dispenser, with a removable cover sheet omitted and with a porous diffuser layer of the dispenser shown laterally exploded away from a base of the dispenser.

Porous diffuser layer 140 may be conveniently provided as a sheet as shown in exemplary embodiment in FIGS. 3 and 5. Such a sheet may be a film (e.g., a microperforated film, with a microperforation being a through-hole having an average diameter of 400 microns or less), a knitted or woven material, etc. In particular embodiments, diffuser layer 140 is a nonwoven sheet (web). Such a sheet may thus comprise a number of specific through-holes that pass directly through the thickness of the sheet (e.g. in the case of a microperforated film); or, a sheet (e.g. a nonwoven) may comprise tortuous paths (e.g., defined collectively by numerous fibers) through the thickness dimension thereof. Either arrangement (or any combination thereof) may be used as long as the ability to permit passage of vapors therethrough (and the ability to deny flow of liquids therethrough, if desired) is achieved. It will be appreciated that the size (e.g., diameter or effective diameter for circular or non-circular microperforations) or effective size of air-filled passages, as well as the chemical composition of the material of diffuser layer 140, may be chosen to achieve the desired combination of properties. Surface treatments and the like may be used to modify e.g. the surface energy of the microperforations, or of fibers that define a tortuous path, to similar ends.

In particular embodiments, a diffuser layer 140 may be hydrophobic, e.g. by virtue of the composition of the material(s) that makes up the diffuser layer, by virtue of surface treatment, coating or the like that is provided on at least some surfaces of the diffuser layer, or by some combination of these. Such a property may render the diffuser layer resistant to being penetrated e.g. by hydrophilic liquid components of a fragrance source 250 that is in the form of e.g. an aqueous gel. Similarly, in some embodiments, a diffuser layer 140 may be oleophobic (again either through the composition of the material that makes up the diffuser layer, by a surface treatment or coating, or the like). Such a property may render the diffuser layer resistant to being penetrated e.g. by hydrophobic liquid components of a fragrance source that is in the form of e.g. an oil-based gel.

The microperforation size (and/or the effective size of a tortuous path) and/or density of microperforations/paths per unit area of diffuser layer 140 may be tailored to provide a desirable fragrance release rate. Exemplary perforation sizes of microperforated films may be e.g. from about 10 to about 100 microns in diameter (or equivalent diameter in the case of non-circular or irregular microperforations). A nonwoven or woven diffuser layer 140 may be optimized e.g. by controlling fiber diameter, basis weight and solidity and/or thickness, to achieve the desired properties. Such nonwovens may be produced by different methods, such as spunbonds, meltblown, airlaying, wetlaying (e.g. paper-making methods), composite methods such as spunbond-meltblown-spunbond (SMS), and so on. Film materials and/or fibers of a woven or nonwoven fibrous layer may be chosen from any suitable material, e.g. polyolefins such as polyethylene and polypropylene, polyvinyl chloride, polyester, polyurethane, cellulosics, and so on. In at least some embodiments, diffuser layer 140 is not a rupturable membrane that is configured to be ruptured to initiate the release of fragrance therethrough. Potentially suitable materials may be chosen from e.g. materials available from Midwest Filtration (Cincinnati, Ohio) under the trade designation UNITHERM.

The ability of a porous diffuser layer 140 to allow passage of gases and vapors through the interstitial spaces thereof in order to completely pass through the thickness of the layer, may be characterized by any suitable parameter or test method. One convenient screening measurement that may correlate with the ability of a material to serve as a porous diffuser layer 140 is an air permeability test (a "Frazier" test) as performed using equipment of the general type supplied by the Frazier Precision Instrument Company (Hagerstown, Md.). Such testing may be performed in general accordance with the methods outlined in ASTM Test Method D737-04 (2012), using 0.5 inches of water pressure drop, a 2.75 inch diameter opening and an 11 mm or 16 mm orifice. In various embodiments, porous diffuser layer 140 may exhibit an air permeability of at least about 100, 200 or 300 cubic feet per minute per square foot. In further embodiments, porous diffuser layer 140 may exhibit an air permeability of at most about 800, 600, 500, or 400 cubic feet per minute per square foot.

Potentially suitable candidate diffuser layers may be tested for their actual release of fragrance, e.g. using a representative fragrance compounded in a suitable nonvolatilizable carrier and loaded into receptacles of a dispenser to which is attached the diffuser layer. The dispenser can be held in a controlled environment, e.g. at 21° C. (or at a higher temperature (e.g. 55° C.) for accelerated testing) and the amount and rate of weight loss from the receptacles can be monitored.

As evident in the exemplary arrangement of FIG. 5, in some embodiments porous diffuser layer 140 comprises a plurality of individually removable sectional areas (e.g., 150*a-f*) each of which respectively occlusively overlies at least a portion of a major open end 116 of the at least one receptacle (e.g., of any of receptacles 112*a-f*). In other words, an individually removable sectional area 150 will at least partially coincide with a respective area 143 (as previously described herein) that occlusively overlies a major open end 116 of a receptacle 112.

At least selected sectional areas 150 of porous diffuser layer 140 are individually removable from the remaining areas (e.g. area 163) of porous diffuser layer 140 (remaining areas 163 may remain in place on base 110 after removal of one or more areas 150). Removal of a selected area 150 thus serves to uncover at least a portion of a major open end 116 of a receptacle 112 that the selected sectional area occlusively overlay prior to its removal. By "uncover" is meant that volatilizable fragrance emitted from that portion of receptacle 112 no longer has to pass through porous diffuser layer 140 to escape dispenser 100; it does not require that the portion of receptacle 112 no longer has any layer overlying it. For example, as discussed in detail later herein, in some embodiments a secondary diffuser 180 may be present through which fragrance still has to pass even though the fragrance does not have to pass through porous diffuser layer 140. Moreover, the act of uncovering a major open end of a receptacle does not require that the entire area of the open end must be completely uncovered (in other words, a removable area 150 does not necessarily have to coincide with the entirety of a respective area 143).

The act of removing a selected area 150 from porous diffuser layer 140 will create an opening in the area of porous diffuser layer 140 formerly occupied by the selected area, through which volatilizable fragrance can now pass at a rate that is not limited by porous diffuser layer 140. In some embodiments selected areas 150 are removed by being completely physically separated from the remaining areas of porous diffuser layer 140. However, in other embodiments a selected area 150 may merely be separated from remaining areas of porous diffuser layer 140 e.g. along several sides of the selected area 150, and may remain connected to at least one remaining area of porous diffuser layer 140 (e.g. by a frangible connection as discussed below). The concept of a "removable" area thus does not require that the removable area must necessarily be completely physically separated from the remaining area of porous diffuser layer 140 in the act of removing the area, although in some embodiments this can be done.

It will be appreciated that the arrangements presented herein allow that one or more selected sectional areas can be individually removed from the porous diffuser layer to uncover at least a portion of a receptacle that the selected sectional area formerly occlusively overlay, without uncovering any portions of other receptacles. For example, with reference to FIG. 5, any one of sectional areas 150*a*-150*f* may be removed from remaining areas (e.g. area 163) of porous diffuser layer 140 so as to respectively uncover a corresponding receptacle of receptacles 112*a*-112*f*, without uncovering any of receptacles 112*a*-112*f* whose overlying sectional area of porous diffuser layer 140 was not removed. Any combination of selected areas may likewise be removed. For example, areas 150*a* and 150*b* may be removed, thus uncovering receptacles 112*a* and 112*b* (which again, only requires that at least portions of the open ends of these receptacles be uncovered), while leaving areas 150*c*-150*f* in place occlusively overlying receptacles 112*c*-112*f*.

It will be appreciated that removing any or all of sectional areas 150 from porous diffuser layer 140 can accelerate the rate of emission of volatilizable fragrance from the receptacle(s) that the sectional area(s) formerly overlay. Any number of individually removable sectional areas, overlying any corresponding number of major open ends of receptacles, may be provided. For example, one, two, three, four, five, six, seven, eight, nine, or ten or more sectional areas (and corresponding receptacles) may be provided (six individually removable sectional areas 150a-150f and six corresponding receptacles 112a-112f are shown in the exemplary embodiment of FIG. 5).

Major open end 116 of each receptacle 112 exhibits an area. In various embodiments, a corresponding removable sectional area 150 that overlies at least a portion of the major open end of the receptacle, may be configured so that removal of the sectional area of the porous diffuser layer uncovers from about 10% to about 100% of the area of the major open end of the receptacle. This can allow an increased rate of emission of fragrance from that particular receptacle, while not allowing accelerated emission of fragrance from any other receptacle that has not been uncovered. As mentioned above, it is not necessary that the entire area of an open end be uncovered in the act of removing a sectional area 150, although this can be done if desired. In some embodiments, sectional areas 150 may be configured so that their removal uncovers at least about 20, 40, 60, or 80% of the area of the major open end of the receptacles that they respectively overlie. In further embodiments, sectional areas 150 may be configured so that their removal uncovers at most about 100, 90, 80, 70, 60, or 50% of the area of the major open end of the receptacles that they respectively overlie. It is not necessary that all of the sectional areas must be identically sized (nor is it necessary that all of the receptacles are identically sized), nor is it necessary that any portion of a removable sectional area is exactly centered over a receptacle, although any of these can be done (as in the exemplary embodiment of FIG. 5) if desired.

Thus in some embodiments, different sectional areas 140 may be of different sizes. In some embodiments, dispenser 100 may include instructions for use. In some embodiments such instructions may be provided on a separate document that is packaged with the dispenser, or which may be printed on the packaging. In some embodiments such instructions may be virtual instructions resident on a website to which the user is directed. In some embodiments such instructions may take the form of at least one indicia that is provided on a component of dispenser 100 (e.g., that is printed on a major surface of the base, the porous diffuser layer, or the removable cover sheet). Such indicia e.g. point out the removable sectional area(s) of the porous diffuser layer to a user, and/or may guide the user to remove a smaller sectional area and/or fewer sectional areas in the event that a slight increase in the emission rate of fragrance is desired, or to remove a larger sectional area and/or a greater number of sectional areas in the event that a larger increase in the emission rate of fragrance is desired.

In some embodiments, sectional areas 150 are frangibly connected to remaining areas 163 (and, if desired, to other sectional areas 150) of porous diffuser layer 140 in order that they be removable (e.g., manually removable by a user). Thus in some embodiments individually removable sectional areas 150 of porous diffuser layer 140 may be (when dispenser 100 is supplied to a user) connected to remaining areas 163 of porous diffuser layer 140 by frangible connections that are provided by die cuts 153 that extend through the entire thickness of porous diffuser layer 140 except at periodic bridging locations 156 where the die cuts are interrupted to provide frangible bridges 155 between the sectional areas 150 of porous diffuser layer 140 and remaining areas 163 of porous diffuser layer 140. In some embodiments, die cuts 153 may be conveniently formed in the same act as the die cutting that is performed to generate external edges 157 that define the lateral perimeter and overall shape of porous diffuser layer 140. In other embodiments, die cuts 153 may be generated in a separate action from the die cutting that defines the overall edges of porous diffuser layer 140.

As noted above, in some embodiments at least some periodic bridging locations 154 may be between adjacent edges of individually removable sectional areas 150 of the porous diffuser layer. One such bridging location is shown as location 156 in FIG. 5. Such arrangements may allow e.g. one sectional area to be removed while leaving an adjacent area to remain in place (to be removed later if desired).

In some embodiments, at least selected removable sectional areas 150 may exhibit a major central portion that is e.g. at least generally centered over a major open end of a receptacle, and may further exhibit one or more tab portions 152 (as depicted in FIG. 5) that extend away from the major central portion. Such tab portions 152 may extend toward a neighboring removable sectional area and if desired neighboring tab portions may meet to provide a bridging location 156 as described above. By such arrangements individual areas 150 may be removed singly; or, several such areas (e.g. an entire strip comprising areas 150a-150c) may be removed in a single operation, e.g. without ever separating the individual areas from each other.

In some embodiments, at least one removable sectional area 150 may comprise a tab portion (e.g. area 158 of FIG. 5) that at least slightly protrudes laterally outward past other portions of porous diffuser layer 140, or is otherwise made readily accessible to being grasped by a user of dispenser 100. Such a protruding portion can provide a fingerlift such that a first area to be initially removed (e.g. area 150a of FIG. 5) can be easily grasped.

Figure 6:
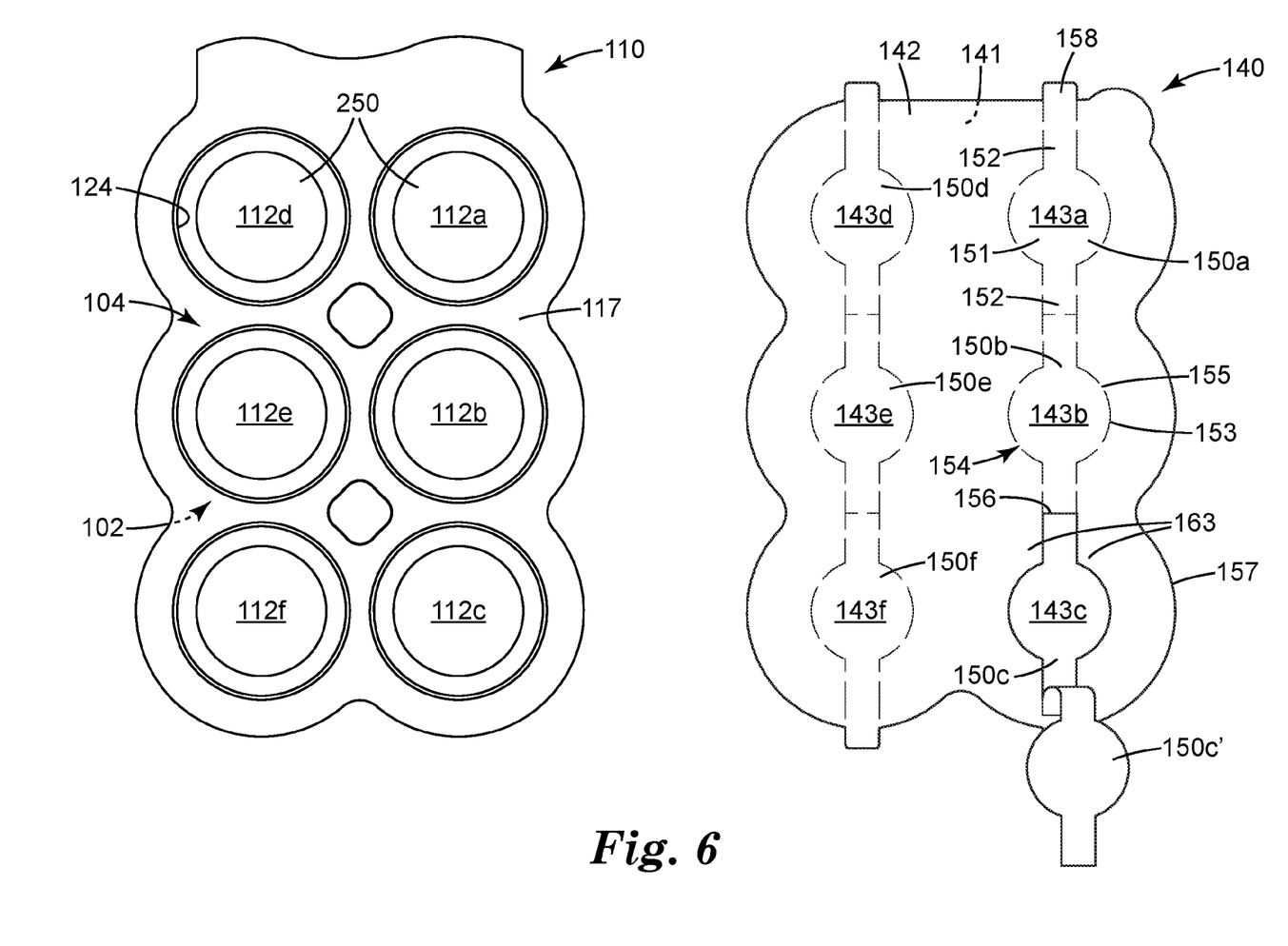
FIG. 6 is a front plan view of the exemplary fragrance dispenser of FIG. 5, with a one individually removable sectional area having been removed.

In some embodiments, one or more individual sectional areas 150 may be removed from porous diffuser layer 140 by being completely physically separated therefrom (and subsequently disposed or recycled). However, it is not necessary that this be done. Thus, in some embodiments a removed sectional area 150 may be left still connected to a remaining area of porous diffuser layer 140. All that is needed is that the area 150 is moved sufficiently that it no longer acts to limit the passage of volatilizable fragrance out of the uncovered area of the receptacle. In other words, an area 150 may be peeled away to uncover at least a portion of a receptacle and left e g "hanging" from an edge of the opening created by the act of removing the selected area. Such an arrangement in is shown in exemplary embodiment in FIG. 6 in which individually removable sectional area 150c has been removed (peeled forwardly) to the position indicated by 150c'.

Figure 7:
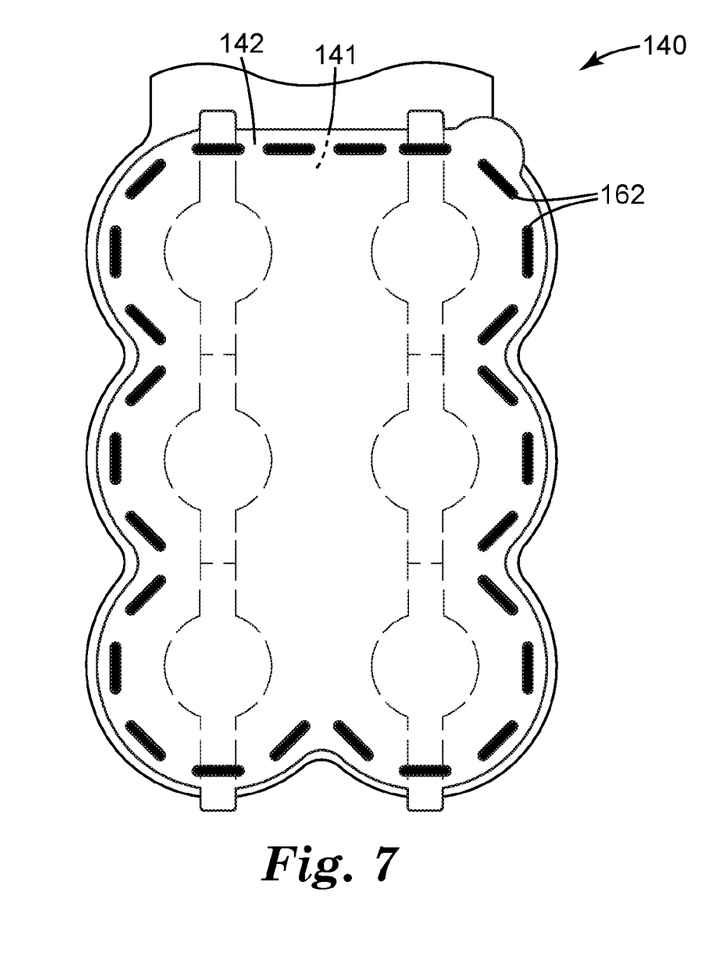
FIG. 7 is a front plan view of an exemplary porous diffuser layer as bonded to an exemplary base.
Figure 8:
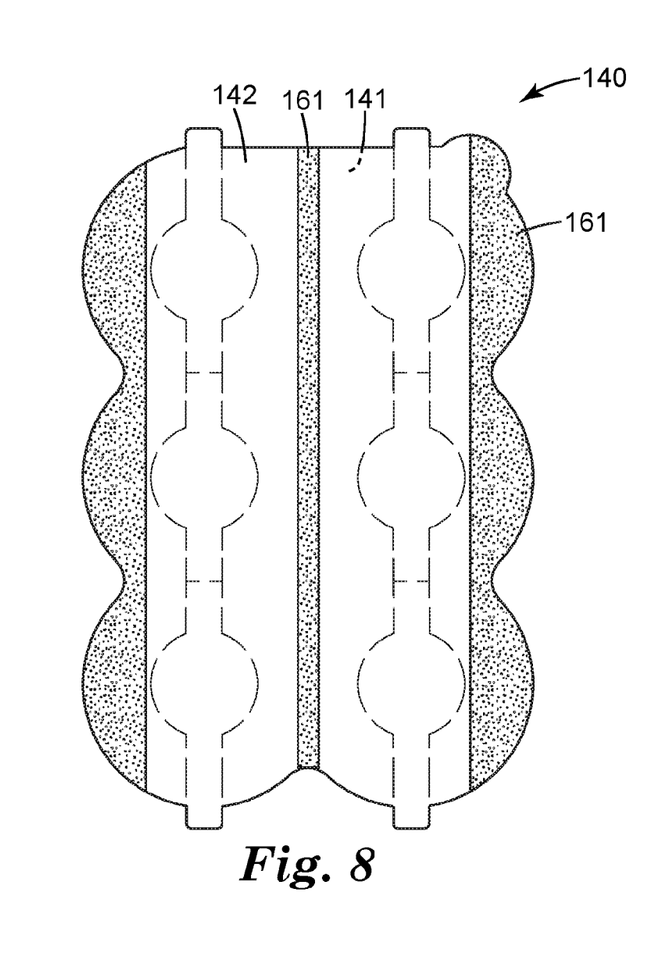
FIG. 8 is a front plan view of an exemplary porous diffuser layer showing a pressure-sensitive adhesive that may be present on a rear surface of the porous diffuser layer.

Porous diffuser layer 140 may be bonded to base 110 (e.g. to front side 140 of main body 111 thereof) in any manner that will allow sectional areas 150 to be removed from layer 140. In some embodiments, this may be performed at least in part by the use of ultrasonic bonds 162 as shown in exemplary embodiment in FIG. 7. In some embodiments such bonds may extend continuously e.g. along the perimeter of main body 111 of base 110 and corresponding areas of porous diffuser layer 140. In other embodiments (e.g. as in the exemplary arrangement of FIG. 7) such bonds may be discontinuous. In some embodiments such bonds may be provided around the perimeter only (again as in FIG. 7); in other embodiments, such bonds may also be present in an interior area of the dispenser (e.g. between row of areas 143*d-f* and row of areas 143*a-c* of FIG. 5). In some embodiments, such bonding may be performed at least in part by the use of a pressure-sensitive adhesive (PSA). Such a PSA may act to enhance the bonding of porous diffuser layer 140 to base 110; or, it may e.g. serve primarily to hold porous diffuser layer 140 in place in the proper position on base 110 until another bonding operation (e.g. ultrasonic bonding) provides the final bond. Such a PSA may be provided at any suitable location. In the exemplary embodiment of FIG. 8, a PSA is provided in the form of two stripes 161 that each extend along a perimeter edge of porous diffuser layer 140, and another stripe 161 that extends along a central portion of layer 140 (e.g. between rows 143*d-f* and 143*a-c* of FIG. 5). All such PSA's will be on the rear surface 141 of porous diffuser layer 140 to facilitate bonding to front side 104 of base 110. (Of course, if desired such a PSA could be initially mounted on front side 104 of base 110 rather than on rear surface 141 of layer 140.) In various embodiments, a PSA may be applied (e.g. as a preformed strip of double-faced adhesive, often referred to as a transfer tape) to rear surface 141 of porous diffuser layer 140 or to front side 104 of base 110; or, a PSA may be formed in place (e.g. by drop-wise digital dispensing, roll coating, hot melt coating, etc. of a PSA precursor) on a desired surface, prior to mating diffuser layer 140 with base 110.

It will be appreciated that it may not be necessary that porous diffuser layer 140 (and e.g. any removable cover sheet 230) must be bonded to base 110 to provide a hermetic seal of individual receptacles 112, although this can be done if desired. Rather, all that is needed is that any leakage pathway left by a non-hermetic seal should be sufficiently small that any loss of volatilizable fragrance from receptacles 112 should be minimal during any initial storage period prior to use of dispenser 100 (e.g., prior to a removable cover sheet 230 being removed to initiate dispensing of fragrance). It has been found that e.g. a non-hermetic combination of PSA and ultrasonic bonding can satisfactorily meet these conditions.

Figure 9:
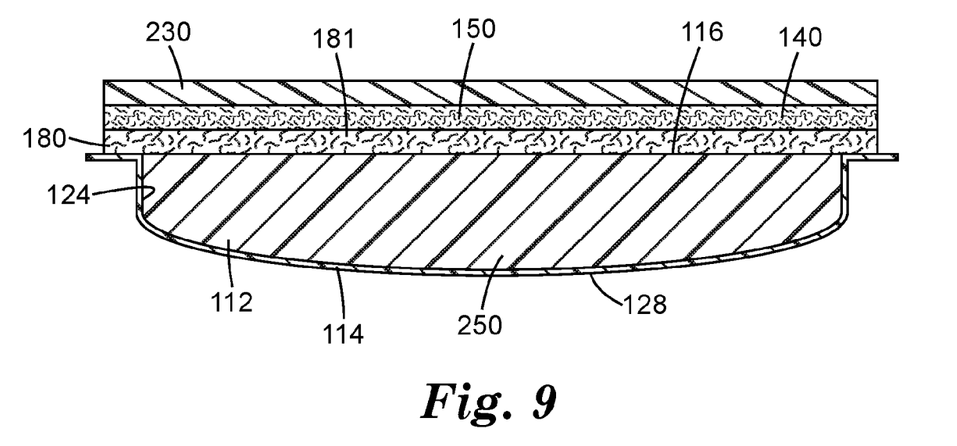
FIG. 9 is an isolated side view in generic representation of an exemplary receptacle of a fragrance dispenser, comprising a secondary diffuser layer, a porous diffuser layer, and a removable cover sheet.

In some embodiments, dispenser 100 may comprise at least one secondary diffuser layer 180. As shown in exemplary embodiment in FIG. 9, a secondary diffuser layer 180, if present, may be sandwiched between porous diffuser layer 140 and base 110. Secondary diffuser layer 180 comprises at least a portion (an area) 181 that is positioned rearward of porous diffuser layer 140 and overlies a receptacle 112. With this arrangement, if a sectional area 150 of porous diffuser layer 140 is removed from a particular receptacle as described above (with cover sheet 230 already having been removed), portion 181 of secondary diffuser layer 180 will be exposed. (In such embodiments, removal of area 150 results in the particular receptacle being "uncovered" as described above, even though portion 181 of secondary diffuser layer 180 will be in the diffusion pathway of the fragrance that is emitted from that receptacle.)

By definition, secondary diffuser layer 180 is more permeable to passage of fragrance therethrough than is porous diffuser layer 140. Specifically, secondary diffuser layer 180 will allow a rate of emission of fragrance from a receptacle 112 that is at least 50% greater than that allowed by the porous diffuser layer 140 (at 21° C.) with which the secondary diffuser layer 180 is used. In further embodiments, secondary diffuser layer 180 will allow an emission rate that is at least 100%, 150%, or 200% greater than that allowed by the porous diffuser layer 140. In some embodiments, individual secondary diffuser layers 180 may be provided for individual receptacles 112. However, it may be convenient that a single secondary diffuser layer 180 be used that includes various portions (areas) that each occlusively overlie a receptacle 112.

A secondary diffuser layer may serve any desired function. In some embodiments, a secondary diffuser layer may limit the rate of emission of fragrance from a receptacle 112, below that which would be allowed in the complete absence of any diffuser layer. In addition to, or instead of this function, a secondary diffuser layer may serve as a physical barrier (but one that is vapor-permeable) to protect fragrance source 250 e.g. from being disturbed, dislodged, or contacted. In addition to, or instead of, either of the above functions, a secondary diffuser layer may serve a decorative or aesthetic function (e.g. to provide less visual contrast upon removal of an area 150 of porous diffuser layer 140). The vapor permeability of secondary diffuser layer 180 may thus be chosen as desired. In some embodiments layer 180 may be comprised of a very open structure (e.g. a very low basis weight nonwoven or scrim, or a polymeric netting or screen) that primarily serves as a physical barrier that does not significantly limit the rate of emission of fragrance from a receptacle. If desired, a secondary diffuser layer 180 may be selected or treated to be at least substantially impermeable to liquids (even while being vapor-permeable) in similar manner as described for porous diffuser layer 140.

In various embodiments, secondary diffuser layer 180 may be chosen from e.g. nonwoven organic polymeric webs, woven or knitted organic polymeric meshes, and organic polymeric nettings or screens. Secondary diffuser layer 180, if present, may be attached to front side 104 of base 110 (and may have porous diffuser layer 140 attached thereto) by any suitable means or mechanism, e.g. by way of PSAs, ultrasonic bonds, and so on.

In some embodiments, a multilayer stack comprising more than one secondary diffuser (e.g. of differing vapor-permeability) may be present. Successive diffuser layers may thus be removed (e.g. peeled off, e.g. starting with porous diffuser layer 140) to achieve a desired rate of emission of fragrance.

In some embodiments, a fragrance dispenser 100 as supplied to a user may comprise a removable cover sheet 230 that overlies the porous diffuser layer 140 at least in the areas where diffuser layer 140 overlies the receptacle(s) 112. In at least some embodiments cover sheet 230 may be impermeable in order to minimize or prevent any emission of fragrance from fragrance source(s) 150 until dispenser 100 is ready to be used, at which time cover sheet 230 may be removed and disposed or recycled. By impermeable is meant that removable cover sheet 230 comprises at least one layer of material that provides (or, comprises layers that collectively provide) that sheet 230 is at least substantially impermeable to volatilizable fragrance. By this is meant that the ratio of the rate at which volatilizable fragrance can leave a receptacle by passing through layer 230 (when layer 230 is in place so as to occlusively overlie the receptacle), to the rate at which the volatilizable fragrance can leave the one receptacle by passing through diffuser layer 140 in the absence of layer 230, is less than 0.001 (at 21° C.). Any suitable material that is sufficiently vapor-impermeable (e.g. polyester film) may be used.

In some embodiments, a single cover sheet 230 may be provided (e.g. in the general manner exemplified in FIG. 4) that can be removed as a unit to initiate the emission of fragrance from all of the receptacles 112. Cover sheet 230 may be removably bonded to diffuser layer 140 in any suitable way that allows at least portions (areas) of cover sheet 230 (or the entirety of cover sheet 230) to be removed by a user (e.g., to be peeled away from diffuser layer 140) to expose porous diffuser layer 140 to initiate the emission of fragrance from one or more receptacles 112 of dispenser 100. In some exemplary embodiments, rear surface 231 of cover sheet 230 may comprise a pressure-sensitive adhesive (e.g., a removable or repositionable PSA) disposed thereon, that allows rear surface 231 of cover sheet 230 to be removably bonded to front surface 142 of diffuser layer 140.

In some embodiments, cover sheet 230 may comprise portions (areas) that are frangibly connected to remaining portions of the cover sheet so that selected portions of cover sheet 230 are each individually removable from the remainder of cover sheet 230. This can allow a user to uncover a particular sectional area of diffuser layer 140 that occlusively overlies a selected receptacle so as to initiate emission of the fragrance from that selected receptacle without initiating emission of fragrance from other receptacles from which overlying portions of cover sheet 230 have not been removed. A user can thus successively remove individual portions of cover sheet 230 (e.g. over hours, days or weeks) to sequentially initiate the emission of fragrance from additional receptacles. In a slight variation of such approaches, two separate, individually-removable cover sheets 230 (e.g., one covering areas 143d-f of porous diffuser layer 140, one covering areas 143a-c of porous diffuser layer 140) can be used. It will be evident that such operations are in addition to the above-described sequential removal of selected sectional areas of porous diffuser layer 140 and can further enhance the dynamic range of user-selectable release rates of fragrance from dispenser 100.

In some embodiments, (e.g. in the event that dispenser 100 is supplied sealed within a vapor-impermeable impermeable package) cover sheet 230 may not necessarily serve to seal receptacles 112 to prevent emission of fragrance therefrom. In such embodiments cover sheet 230 may e.g. serve primarily to protect porous diffuser layer 140 from physical damage, and/or may serve a decorative function. In such cases, cover sheet 230 may be made of any suitable material.

Fragrance source 250 may include any suitable volatilizable fragrance or any combination of two or more fragrances. Such a fragrance may be chosen to impart a pleasing odor, to mask odors that are perceived as undesirable, and so on. A volatilizable fragrance may be any molecule or mixture of different molecules that is chosen to impart a pleasing odor, to may mask odors that are perceived as undesirable, and so on. Any such molecule may be chosen from those compounds commonly referred to as perfumes, aroma compounds, aromatherapy compounds, odorants, flavors, essential oils, and so on. Such molecules will exhibit the appropriate vapor pressure at the temperatures usually encountered in e.g. residential HVAC systems (e.g., 18-25° C.) to function as desired. In various embodiments, a volatilizable fragrance may comprise a molecular weight (of a single molecule) or an average molecular weight (for mixtures of molecules of different molecular weights), of less than about 500, 400, 300, or 200. Various volatilizable fragrances and categories thereof are disclosed in U.S. Pat. No. 8,043,606 to MacBeath, which is incorporated by reference herein. Potentially suitable fragrances are available e.g. from International Flavors and Fragrances (New York City, N.Y.) and J&E Sozio Descollonges SAS (Paris, France). In particular embodiments in which an array of receptacles 112 is present, different fragrances and/or mixtures thereof may be present in the various receptacles, as desired.

In some embodiments, fragrance source 250 may comprise one or more volatilizable fragrances as neat fragrance liquids unmixed with any other material. (It is noted however that many fragrances may themselves be mixtures of numerous molecules.) In many embodiments, however it may be convenient to mix the at least one volatilizable fragrance with at least one nonvolatilizable carrier material (with the term nonvolatilizable meaning that in use of fragrance dispenser 100, the ratio of the rate at which the carrier material exits a receptacle through the diffuser layer to the rate at which the volatilizable fragrance exits, is less than 0.001.)

A nonvolatilizable carrier material may be chosen from any suitable material. In various embodiments, such a carrier material may comprise an organic polymeric material (which, in this context, includes e.g. waxes, oils, etc. as long as such materials provide acceptable properties). Such a carrier material may advantageously provide that fragrance source 250 is in the form of a viscous liquid, gel, grease, jelly, semi-solid, wax, or the like (noting that there may not necessarily be a firm dividing line between some of these categories), in the typical temperature ranges at which the fragrance dispenser is used. (The latter temperatures are often in the range of those found in a typical conditioned space; e.g. between 18 and 25° C.)

In further detail, a nonvolatilizable carrier (e.g., a polymeric material) may provide a matrix for dispersal of the fragrance thereinto. In some embodiments, the at least one volatilizable fragrance and the at least one nonvolatilizable carrier material may be mixed with each other to form a solution (i.e., so that substantially no parcels of non-dissolved volatilizable fragrance are present). Exemplary organic polymers that may find use as nonvolatilizable carriers include e.g. olefinic copolymers, e.g. copolymers of polyethylene with ethylene methyl acrylate (for example the resins available from Exxon Mobil under the trade designations OPTEMA 120 and 220), ethylene vinyl acetate (EVA), or other copolymers containing other functional groups such as acids, esters, amides, acrylates, and the like. In addition, the organic polymer system could be comprised of styrene-isoprene-styrene segments or styrene-butadiene-styrene segments such as those seen in Kraton thermoplastic elastomer systems. Fragrance source 250 may comprise (either instead of, or in addition to, any nonvolatilizable organic polymer that may be present) any suitable inorganic material such as e.g. clay, fumed silica, diatomaceous earth, silica aerogels, and so on.

Fragrance source 250 may also comprise any other agent as desired to change the viscosity, tackiness or any other characteristic of the fragrance source. (Such agents may be nonvolatilizable or volatilizable.) Viscosity modifiers include plasticizers such as isopropyl myristate, heavy naphthenic oils, or other polymeric systems that may be branched, linear, dendritic, and so on. Tackifiers include Wingtack Plus and the like. If desired, one or more gelling agents may be used, e.g. wax esters such as those available from Croda, Edison, N.J. under the trade designation SYNCROWAX, and acrylate containing polymers, such as those available from Air Products, Allentown, Pa. under the trade designation INTELLIMER. Such components may be used to provide e.g. an oil-based gel. In some embodiments, gelling agents such as e.g. crosslinked polysaccharides, starches, alginates, carrageenan, and the like, may be used to provide a fragrance source in the form of an aqueous or aqueous-containing gel. Any fragrance source may of course comprise any desired combination of hydrophobic and hydrophilic components, for any purpose, as desired. Components of a fragrance source 250 may be chosen so as to render the volatilizable fragrance completely mixed (e.g., solubilized) with the other components without any partitioning or phase separation, and also to prevent or minimize any syneresis of liquid fragrance (or any other component) therefrom. In some embodiments, volatilizable fragrance may be provided in an aqueous carrier, which term generally encompasses solutions of fragrance in water or in mixtures or solutions of water with other diluents (e.g. alcohols, glycol ethers, and so on), which solutions may further include e.g. additives such as gelling agents, viscosifiers, and so on. In various embodiments, fragrance source 250 may exhibit a viscosity at 25° C. of at least about 10, 20, 40, 80, 200, 400, 1000, or 2000 Poise.

In some embodiments, fragrance source 250 may comprise at least one colorant (e.g., dye). A colorant may be volatilizable (e.g. guaiazulene dye) e.g. with an evaporation rate similar to that of the volatilizable fragrance, so that release of the dye from the fragrance source causes a color change in the fragrance source that is commensurate with the depletion of fragrance from the fragrance course. Or, a colorant may be nonvolatilizable, and the nonvolatilizable colorant, the volatilizable fragrance, and e.g. the nonvolatilizable carrier material may be chosen in combination so that release of the fragrance from the fragrance source causes the color of the fragrance source to change so that depletion of the fragrance from the fragrance source can be monitored. In either case, at least a portion of base 110 that defines a major closed end 114 of a receptacle 112 may be at least translucent or transparent, so that any change in color of the fragrance source may be visually observed through the base.

The volatilizable fragrance can be combined with the nonvolatilizable carrier material (and with any other component) in any desired ratio. In various embodiments, the volatilizable fragrance may comprise at least about 30, 50, 60, 70, 80, or 90 wt. % of the fragrance source. In further embodiments, the volatilizable fragrance may comprise at most about 90, 80, 70, 60, 50, or 40 wt. % of the fragrance source. The fragrance may be combined with other components, e.g. a nonvolatilizable carrier, by batch mixing, by compounding in an extruder, or in general by any process that sufficiently disperses or homogenizes the fragrance within the matrix. The compounded mixture may be loaded into a receptacle or receptacles to therein provide a fragrance source. If desired, the compounded mixture may be heated slightly to facilitate loading of the mixture into a receptacle.

In some embodiments, fragrance source 250 may occupy at least about 70, 80, 90, 95, or 98 volume percent of the receptacle volume, the receptacle volume being defined in combination by the open-ended receptacle 112 (e.g., by the downstream surfaces of the molded depression 128) and the overlying diffuser layer 140. In specific embodiments, at least a portion of a downstream major surface of fragrance source 250 is in intimate contact with an upstream surface of diffuser layer 140. In some embodiments, the receptacle may include a space-filling network of solid material (e.g. an open-cell foam, a reticulated foam, a nonwoven, a netting, a collection of particulates or the like) that is not solubilizable by the liquid fragrance and that occupies a portion of the receptacle volume and comprises numerous open-ended cavities that may collectively provide a reservoir for the fragrance source. If desired, a fragrance source may be pre-loaded into a space-filling network, which network is then placed into a receptacle 112 that is sized and shaped to accept the space-filling network. Exemplary foams may be constructed out of polyethylene, polyurethane, PVC and the like. Exemplary nonwovens and particulates may be those that are manufactured to be sorbents, such as those manufactured for chemical spill clean up, e.g., 3M Petroleum Sorbent pads available from 3M Company, St. Paul, Minn. In at least some embodiments, fragrance source 250 as provided in receptacle 112, is not contained within any kind of secondary container or barrier, in particular a rupturable barrier, within receptacle 112.

It will thus be appreciated that fragrance source 250 can encompass any desired method of providing volatilizable fragrance within a receptacle 112. In some embodiments, fragrance source 250 may take the form of a flowable liquid, e.g. a neat liquid fragrance. In some embodiments, volatilizable fragrance may be e.g. compounded with a carrier so as to be present in a receptacle 112 in the form of a generally solid (at 21° C.) mass (e.g., a wafer or puck of any desired shape and aspect ratio). It will be appreciated that this may allow the most freedom to position dispenser 100 in any desired orientation (e.g. vertical) without encountering any possibility of any component (e.g. a liquid component) of the fragrance source inadvertently leaking out of a receptacle. (Such considerations may of course be largely moot in embodiments in which porous diffuser layer 140 (and/or secondary diffuser layer 180 if present) is impermeable to passage of liquids therethrough.)

It is emphasized that a "fragrance" as referred to herein is a molecule (or mixture of molecules) that is chosen for the specific purpose of imparting a pleasing odor to an ambient environment or masking undesirable odors in such an environment. In other words, a molecule does not qualify as a fragrance as disclosed herein, merely because it may exhibit a discernable odor that is incidental to the properties and use of the molecule. By way of specific example, an isopropyl alcohol-impregnated dressing for medical use would not qualify as a fragrance as disclosed herein. Similarly, a pouch or sachet that such an alcohol-containing dressing is packaged in, would not qualify as a fragrance dispenser as disclosed herein.

It is also emphasized that terms such as "volatilizable" and "volatilized" are used broadly to denote that fragrance that is emitted from a fragrance source 250 moves (e.g. through any or all of a porous diffuser layer 140, a secondary diffuser layer 180, and/or an empty airspace formerly occupied by a porous diffuser layer) as molecules in vapor form, rather than in liquid or solid form (e.g. in the form of aerosol droplets, sprayed liquid or solid particles, and so on). The particular process by which the fragrance is liberated from fragrance source 250 is not limited and may include e.g. evaporation, sublimation, or a mixture of the two. Still further, although the term "diffuser" layer has been used for convenience of description, this does not imply that the passage of a fragrance out of a fragrance source 250 and away from dispenser 100 must occur strictly by molecular diffusion (e.g., Fickian diffusion). While such a mechanism may operate at least in part e.g. during passage of fragrance through interstitial air spaces of a porous layer, such a mechanism is not required to be the only mechanism by which fragrance is emitted from dispenser 100. In fact, in some embodiments molecular diffusion may not be the primary mechanism, e.g. it may be dominated by some other mechanism. For example, the rate of emission of fragrance from fragrance source 250 may be significantly increased in the event that dispenser 100 is exposed to airflow, in comparison to the emission rate when dispenser 100 is positioned in quiescent air.

It will be appreciated based on the disclosures herein that providing porous diffuser layer 140 with multiple sectional areas 150 that are individually removable from remaining areas of layer 140, can significantly enhance the ability of the rate of release of fragrance from dispenser 100 to be selected and customized as desired by a user. This is particularly advantageous in view of the fact that humans have any ability to smell different substances over a very wide dynamic range and that the ability to perceive an odor is subject to habituation. This being the case, the preferred level of fragrance (as achieved by emitting fragrance at a desired rate from a dispenser) may vary very widely between different persons. In the present work it has been found that providing a porous diffuser layer 140 with multiple individually removable sectional areas as disclosed herein can advantageously allow the release rate of fragrance to be varied over a wide range.

For example, one user may simply remove cover sheet 230 (in its entirety) to initiate the emission of fragrance, while leaving porous diffuser layer 140 in its as-supplied condition (that is, without removing any of the individually removable sectional areas 150 over the lifetime of the dispenser). Another user may likewise remove cover sheet 230 in its entirety and may also remove one or more of the individual sectional areas of porous diffuser layer 140 to accelerate the emission of fragrance from one or more selected receptacles. Such a user might e.g. remove individual sectional areas at regular intervals (e.g., one per day, one per week, etc.) in order to achieve a desired rate of emission of fragrance. Still another user may (after removing the cover sheet) initially remove half of the individual sectional areas of porous diffuser layer 140 and may then remove the remaining individual sectional areas after a given time interval. Another user may remove the cover sheet and immediately remove all of the individual sectional areas of porous diffuser layer 140 thus achieving the highest possible release rate of fragrance. It is evident that a wide variety of individual preferences can be accommodated.

Moreover, the above examples have concerned embodiments in which the rate of emission of fragrance can be accelerated (by removing individual sectional areas of diffuser layer 140) above a "baseline" rate that exists when all of the receptacles are emitting fragrance through diffuser layer 140. As disclosed earlier herein, the rate of emission of fragrance can, if desired, be manipulated to be below this "baseline" rate, by the use of a cover sheet 230 that is itself removable in portions rather than being removable only its entirety. That is, rather than the entire cover sheet 230 being removed at initial use of dispenser 100, in some embodiments only selected portions of the cover sheet may be removed to initiate emission of fragrance from the corresponding receptacles. Additional portions of the cover sheet may be removed at desired time intervals. It will be appreciated that such arrangements can further enhance the dynamic range of the rate at which fragrance can be dispensed by dispenser 100, which can further enhance the ability to tailor the performance of the dispenser as desired by particular individuals.

Fragrance dispenser 100 may be used to emit fragrance into an ambient environment, in any suitable location. Some uses may involve exposing the dispenser to a stream of moving air (e.g. as motivated by a fan or blower), as discussed in detail below. Other uses may involve placing the dispenser in an ambient environment that does not involve a stream of moving air (other than e.g. stray air currents, wind, and so on). For example, a dispenser may simply be placed in a room (e.g. hung vertically from a wall, laid flat on a shelf, etc.), a vehicle, and so on. In particular embodiments a dispenser may be positioned in a window (e.g. attached to a window screen) to take advantage of wind impinging thereon.

In some embodiments, dispenser 100 may be itself moved through air (e.g. quiescent air). For example, a dispenser 100 may be mounted to a blade or hub of a fan (e.g. a ceiling fan), mounted to a door that is opened and closed frequently, mounted to a floor-cleaning robot or a vacuum cleaner, and so on. It is thus apparent that in such embodiments, dispenser 100 may be mounted to any item that can be moved relative to surrounding air.

In some embodiments, a dispenser 100 may be exposed to a stream of moving air that is motivated by a fan or blower rather than by e.g. wind. It is not necessary that the dispenser actually be physically located anywhere near the fan or blower. For example, in some embodiments a dispenser 100 may be positioned proximate an air-emitting vent of a vehicle climate-control system or a building HVAC system. (For example, a dispenser could be attached to a register, grille or louver of such a vent.) Or, a dispenser may be positioned proximate an intake (air-return) unit of a building HVAC system (recognizing that in such a case the fragrance emitted from the dispenser will be distributed throughout the entire portion of the building that is served by the HVAC system rather than e.g. remaining primarily in one room). A dispenser could be placed in the flowpath of a fan (e.g. a window fan, a box fan, an oscillating fan, a ceiling fan, and so on) e.g. by being attached to a protective grille or casing of the fan or by being mounted to a surface (e.g. of a ceiling, floor, wall, table, shelf, stand, etc.) near the fan. Similarly, a dispenser could be placed in the airflow path of a so-called mini-split climate control unit.

It will be appreciated that the rate of emission of fragrance from dispenser 100 may be affected by the velocity and/or volumetric flowrate of air that impinges on the dispenser and may also be affected by temperature. This being the case, the procedures disclosed herein may be modified when dispenser 100 is positioned (e.g. in the summer) in a stream of cooled air of an HVAC system, in comparison to the procedures used when dispenser 100 is positioned (e.g. in the winter) in a stream of heated air from the HVAC system. In some embodiments, the temperature of flowing air that impinges on the dispenser may be purposefully manipulated to affect the rate of emission of fragrance from the dispenser. Similarly, one or more heat sources or cooling sources that do not involve flowing air (e.g. a miniaturized resistive heater, an IR heater, and so on) may be positioned near dispenser 100 to desirably affect the rate of emission of fragrance therefrom.

In some embodiments, a dispenser 100 may be positioned in proximity to (e.g., mounted on) an air filter e.g. of an HVAC unit. In particular embodiments, dispenser 100 may be mounted upstream of such an air filter, e.g. with a "front" face of the dispenser facing toward the air filter. Such uses are described in detail in PCT International Publication No. WO 2016011038 and in corresponding U.S. Provisional Patent Application No. 62/026,112 entitled FRAGRANCE DISPENSER FOR AIR FILTER, both of which are incorporated by reference in their entirety herein.

A dispenser 100 may be mounted on an air filter by way of any suitable mechanism. Many such mechanisms may conveniently make use of a perimeter frame of the air filter (such as made from cardboard, chipboard or the like) for such mounting. In some embodiments base 110 of dispenser 100 may thus comprise a main body 111 that comprises the at least one receptacle 112; and, an extended portion 130 (as shown in exemplary embodiment in FIG. 2, and omitted for clarity in FIGS. 5 and 6) that extends away from the main body. Extended portion 130 may comprise any suitable mounting mechanism configured to mount (attach) to a perimeter frame of an air filter so as to position fragrance dispenser 100 e.g. so that at least some receptacles 112 thereof are proximate an airstream-receiving or airstream-emitting area of the air filter.

In some embodiments, an extended portion 130 may comprise pressure-sensitive adhesive to facilitate attachment of dispenser 100 to any desired object or surface. Instead of or as an adjunct to an adhesive, extended portion 130 may comprise any mechanical mounting/attachment mechanism. For example, a small hole may be provided in extended portion 130 of base 110 of dispenser 100, into which any suitable hook or post can be inserted. It will be understood that this is merely an example and that many mounting attachment systems may be used.

In some embodiments, an extended portion 130 of base 110 may generally comprise an L-shape with a first portion that extends from the main body of base 110 in a direction at least generally along a major plane of the main body of the base, and a second portion that extends from a terminus of the first portion and that is oriented at least generally orthogonally to the first portion.

In some embodiments, an extended portion 130 may comprise first and second portions as described above, and may further comprise a third portion that extends from a terminus of the second portion and that comprises a major plane that is oriented at least generally parallel to a major plane of the first portion. Such an extended portion 130 may thus generally comprise a U-shaped hook that allows dispenser 100 to be hung from any desired object. Of course, similar arrangements may be achieved e.g. with a hook provided by a smoothly arcuate extended portion 130 rather than a U-shaped extended portion 130. Although extended portion 130 and L-shaped and U-shaped variations thereof were described above with particular regard to mounting dispenser 100 to e.g. a frame of a framed air filter, it will be appreciated any such extended portion 130 may be used to mount dispenser 100 to any desired object. Furthermore, it will be appreciated that in some embodiments no extended portion 130 need be present.

In some embodiments, a cover (e.g. a molded plastic cover) may be mounted on the front side of dispenser 100. Such a cover may have e.g. one or more movable (e.g. slidable) portions that can be moved back and forth so as to allow or prevent the emission of volatilizable fragrance from various receptacles. Such a cover may e.g. act as an adjunct to the herein-described removable sectional areas of porous diffuser layer 140 and/or removable portions of a cover sheet 230, in allowing the dispensing rate of fragrance to be customized by a user. For example, in particular embodiments in which different fragrances are present in different receptacles, such a cover can allow a user to switch back and forth between fragrances that are dispensed.

Dispenser 100 may be produced in any desired manner. For example, a fragrance source 250 may be produced by compounding a volatilizable liquid fragrance (which, as noted, may be comprised of a mixture or solution of many different molecules) with a nonvolatilizable carrier, e.g. at elevated temperature. The resulting mixture may then be loaded into individual receptacles 112 of base 110 (and, if loaded at elevated temperature, may then be allowed to cool, e.g. to form a solid wafer). A secondary diffuser layer 180 may be optionally bonded to the front side 104 of main body 111 of base 110 if desired. A porous diffuser layer 140 is bonded to the front side 104 of main body 111 of base 110 (or to the front side of secondary diffuser layer 180 if a layer 180 is present and if it e.g. extends as far toward the perimeter of the base as does layer 140). In various embodiments, such bonding may be facilitated by a pressure-sensitive adhesive (PSA) that is disposed on bonding areas of major rear surface 141 of layer 140; such bonding may be by way of ultrasonic bonding; or, a combination of both may be used. A removable cover sheet 230 may be removably bonded (e.g. by way of a PSA) to the front surface 142 of porous diffuser layer 140. In some embodiments, cover sheet 230 may be bonded to porous diffuser layer 140 before either of these components is bonded to the main body of the base. Such an approach allows layers 230 and 140 to be pre-laminated to each other so that they can be bonded to the base as a single unit. (In such a case, if porous diffuser layer 140 is to be ultrasonically bonded to the base, the composition of cover sheet 230 may be chosen so that ultrasonic energy can be transmitted through layer 230 without damaging layer 230). In embodiments in which a secondary diffuser layer 180 is to be present, layer 180 and layers 140 and 230 can all be laminated together to form a three-layer pre-laminated stack that can be bonded to base 110 as a unit, if desired.

Once produced, dispenser 100 can be packaged in any suitable package. In particular embodiments the packaging material may be chosen (e.g., the packaging material may be a metallized polyester) to provide a sealed package from which minimal loss of fragrance may occur even over long-term storage and/or exposure to elevated temperatures. In some embodiments in which dispenser 100 is packaged (i.e. sealed) within a packaging material with appropriate vapor-barrier properties, cover sheet 230 may not need to exhibit significant vapor-barrier properties; in particular embodiments of this type, cover sheet 230 may be omitted from dispenser 100.

LIST OF EXEMPLARY EMBODIMENTS

Embodiment 1 is a fragrance dispenser comprising: a base comprising at least one receptacle with a major closed end and a major open end; a porous diffuser layer comprising at least one sectional area that occlusively overlies at least a portion of a major open end of a receptacle; and, a fragrance source provided within at least a portion of the at least one receptacle and that comprises at least one volatilizable fragrance, wherein the at least one sectional area of the porous diffuser layer is removable from remaining portions of the porous diffuser layer to uncover at least a portion of a receptacle that the at least one sectional area occlusively overlies.

Embodiment 2 is the fragrance dispenser of embodiment 1 wherein the porous diffuser layer is an organic polymeric nonwoven web that exhibits an air permeability of from about 200 to about 800 cubic feet per minute per square foot.

Embodiment 3 is the fragrance dispenser of any of embodiments 1-2 wherein the porous diffuser layer is permeable to vapors but is at least substantially impermeable to liquids.

Embodiment 4 is the fragrance dispenser of any of embodiments 1-3 wherein the porous diffuser layer is bonded to the base by a pressure-sensitive adhesive that is provided along portions of a perimeter of the porous diffuser layer, and by discrete ultrasonic welds that are provided along portions of the perimeter of the porous diffuser layer.

Embodiment 5 is the fragrance dispenser of any of embodiments 1-4 further comprising a secondary diffuser layer that: is at least 50% more permeable to passage of fragrance therethrough than is the porous diffuser layer; does not comprise any removable sectional areas; and is sandwiched between the porous diffuser layer and the base, wherein the porous diffuser layer and the secondary diffuser layer are configured so that upon removal of a sectional area of the porous diffuser layer, a portion of the secondary diffuser layer that overlies a receptacle of the base is exposed.

Embodiment 6 is the fragrance dispenser of embodiment 5 wherein the secondary diffuser layer is chosen from the group consisting of a nonwoven organic polymeric web, a woven or knitted organic polymeric mesh, and an organic polymeric netting or screen.

Embodiment 7 is the fragrance dispenser of any of embodiments 1-6 wherein the base is made of a thermoplastic organic polymeric resin that is at least substantially impermeable to liquids and vapors and wherein each receptacle is provided by a thermoformed depression in the base, wherein a terminus of the depression provides the major closed end of the receptacle and wherein a major open end of the depression provides the major open end of the receptacle.

Embodiment 8 is the fragrance dispenser of any of embodiments 1-7 wherein the base comprises a main body that comprises the at least one receptacle and wherein the base further comprises an extended portion that extends away from the main body and that comprises a mounting mechanism.

Embodiment 9 is the fragrance dispenser of any of embodiments 1-8 wherein the fragrance source is chosen from the group consisting of neat liquid fragrance, liquid fragrance mixed with a nonvolatilizable diluent liquid, liquid fragrance in aqueous solution, and a liquid fragrance sorbed into interstices of a porous insoluble solid matrix material.

Embodiment 10 is the fragrance dispenser of any of embodiments 1-9 wherein the fragrance source is a liquid fragrance that is mixed and solubilized with a nonvolatilizable matrix material that is a solid at room temperature and that is solublizable by the liquid fragrance, and wherein the fragrance-matrix mixture is in the form of a solid wafer when at 21° C.

Embodiment 11 is the fragrance dispenser of any of embodiments 1-10 wherein the liquid fragrance makes up at least about 80 wt. % of the fragrance source.

Embodiment 12 is the fragrance dispenser of any of embodiments 1-11 comprising: a base comprising a plurality of receptacles each with a major closed end and a major open end; a porous diffuser layer comprising sectional areas each of which occlusively overlies at least a portion of a major open end of a receptacle of the plurality of receptacles; and, a fragrance source provided within at least a portion of each receptacle and that comprises at least one volatilizable fragrance, wherein at least selected sectional areas of the porous diffuser layer are each individually removable from the porous diffuser layer to uncover at least a portion of a receptacle that the selected sectional area occlusively overlies.

Embodiment 13 is the fragrance dispenser of embodiment 12 wherein the base comprises at least six receptacles and wherein the porous diffuser layer comprises at least six sectional areas that respectively occlusively overlie at least a portion of a major open end of each of the six receptacles, which six sectional areas are each frangibly connected to remaining areas of the porous diffuser layer so that the six sectional areas are each individually removable from the porous diffuser layer.

Embodiment 14 is the fragrance dispenser of any of embodiments 12-13 wherein the major open end of each receptacle exhibits an area and wherein a sectional area of the porous diffuser layer that is individually removable from the porous diffuser layer, is configured so that removal of the sectional area of the porous diffuser layer uncovers from about 10% to about 100% of the area of the major open end of the receptacle that the sectional area of the porous diffuser layer occlusively overlies so as to allow accelerated emission of fragrance from that receptacle, while not allowing accelerated emission of fragrance from any other receptacle.

Embodiment 15 is the fragrance dispenser of any of embodiments 12-14 wherein the major open end of each receptacle exhibits an area and wherein a sectional area of the porous diffuser layer that is individually removable from the porous diffuser layer, is configured so that removal of the sectional area of the porous diffuser layer uncovers from about 40% to about 60% of the area of the major open end of the receptacle that the sectional area of the porous diffuser layer occlusively overlies.

Embodiment 16 is the fragrance dispenser of any of embodiments 12-15 wherein the individually removable sectional areas of the porous diffuser layer are frangibly connected to remaining areas of the porous diffuser layer by frangible connections that are provided by die cuts that extend through the entire thickness of the porous diffuser layer except at periodic bridging locations where the die cuts are interrupted to provide frangible bridges between the individually removable sectional areas of the porous diffuser layer and the remaining areas of the porous diffuser layer.

Embodiment 17 is the fragrance dispenser of embodiment 16 wherein at least some of the periodic bridging locations are between adjacent edges of individually removable sectional areas of the porous diffuser layer.

Embodiment 18 is the fragrance dispenser of any of embodiments 12-17 further comprising a removable cover sheet that overlies, and is removably adhesively bonded to, the porous diffuser layer; and, that comprises at least selected portions that are peelably detachable from the porous diffuser layer to expose the porous diffuser layer to initiate dispensing of the fragrance.

Embodiment 19 is the fragrance dispenser of embodiment 18 wherein at least selected portions of the removable cover sheet are frangibly connected to remaining portions of the removable cover sheet so that the selected portions of the cover sheet are each individually removable from remaining portions of the removable cover sheet to uncover a selected sectional area of the porous diffuser layer that occlusively overlies a selected receptacle to initiate dispensing of the fragrance from that selected receptacle without initiating dispensing of fragrance from other receptacles.

Embodiment 20 is the fragrance dispenser of any of embodiments 18-19 wherein the dispenser comprises at least one indicia printed on a major surface of the base, of the porous diffuser layer, or of the removable cover sheet.

Embodiment 21 is a method of dispensing fragrance into an atmosphere, the method comprising: positioning a fragrance dispenser of any of embodiments 1-20 in the atmosphere; if a removable cover sheet is present, removing at least a selected portion of the removable cover sheet from the fragrance dispenser; and, optionally removing at least one selected section of the porous diffuser layer to uncover an area of a major open end of a receptacle that the porous diffuser layer occlusively overlaid before being removed, to allow accelerated emission of fragrance from that receptacle.

Embodiment 22 is the method of embodiment 21 wherein the method comprises sequential removal of selected sections of the porous diffuser layer, the sequential removals being spaced over a period of at least one day.

Embodiment 23 is the method of any of embodiments 21-22 wherein the method comprises sequential removal of selected portions of the removable cover sheet, the sequential removals being spaced over a period of at least one day.

Embodiment 24 is the method of any of embodiments 21-23 wherein the fragrance dispenser is positioned in a quiescent air environment in a location chosen from the group consisting of an interior of a room of a building and an interior of a vehicle.

Embodiment 25 is the method of any of embodiments 21-23 wherein the fragrance dispenser is positioned in an airflow path in a location chosen from a group consisting of a position proximate an air filter of an HVAC system, a position proximate an air filter of a room air purifier, a position proximate an air filter of a vehicle, a position proximate a motorized fan, a position proximate an air vent of an HVAC system, and a position proximate an air vent of a vehicle climate-control system.

It will be apparent to those skilled in the art that the specific exemplary elements, structures, features, details, configurations, etc., that are disclosed herein can be modified and/or combined in numerous embodiments. All such variations and combinations are contemplated by the inventor as being within the bounds of the conceived invention, not merely those representative designs that were chosen to serve as exemplary illustrations. Thus, the scope of the present invention should not be limited to the specific illustrative structures described herein, but rather extends at least to the structures described by the language of the claims, and the equivalents of those structures. Any of the elements that are positively recited in this specification as alternatives may be explicitly included in the claims or excluded from the claims, in any combination as desired. Any of the elements or combinations of elements that are recited in this specification in open-ended language (e.g., comprise and derivatives thereof), are considered to additionally be recited in closed-ended language (e.g., consist and derivatives thereof) and in partially closed-ended language (e.g., consist essentially, and derivatives thereof). Although various theories and possible mechanisms may have been discussed herein, in no event should such discussions serve to limit the claimable subject matter. To the extent that there is any conflict or discrepancy between this specification as written and the disclosure in any document incorporated by reference herein, this specification as written will control.

What is claimed is:

1. A fragrance dispenser comprising:
   a base comprising at least one receptacle with a major closed end and a major open end;
   a porous diffuser layer comprising at least one sectional area that occlusively overlies at least a portion of a major open end of a receptacle, wherein the porous diffuser layer is an organic polymeric nonwoven web that exhibits an air permeability of from about 200 to about 800 cubic feet per minute per square foot; and,
   a fragrance source provided within at least a portion of the at least one receptacle and that comprises at least one volatilizable fragrance,
      wherein the at least one sectional area of the porous diffuser layer is removable from remaining portions of the porous diffuser layer to uncover at least a portion of a receptacle that the at least one sectional area occlusively overlies.

2. The fragrance dispenser of claim 1 further comprising a secondary diffuser layer that:
   is at least 50% more permeable to passage of fragrance therethrough than is the porous diffuser layer;
   does not comprise any removable sectional areas; and
   is sandwiched between the porous diffuser layer and the base,
      wherein the porous diffuser layer and the secondary diffuser layer are configured so that upon removal of a sectional area of the porous diffuser layer, a portion of the secondary diffuser layer that overlies a receptacle of the base is exposed.

3. The fragrance dispenser of claim 2 wherein the secondary diffuser layer is chosen from the group consisting of a nonwoven organic polymeric web, a woven or knitted organic polymeric mesh, and an organic polymeric netting or screen.

4. The fragrance dispenser of claim 1 wherein the base is made of a thermoplastic organic polymeric resin that is at least substantially impermeable to liquids and vapors and wherein each receptacle is provided by a thermoformed depression in the base, wherein a terminus of the depression provides the major closed end of the receptacle and wherein a major open end of the depression provides the major open end of the receptacle.

5. The fragrance dispenser of claim 1 wherein the fragrance source is chosen from the group consisting of neat liquid fragrance, liquid fragrance mixed with a nonvolatilizable diluent liquid, liquid fragrance in aqueous solution, and a liquid fragrance sorbed into interstices of a porous insoluble solid matrix material.

6. The fragrance dispenser of claim 1 wherein the fragrance source is a liquid fragrance that is mixed and solubilized with a nonvolatilizable matrix material that is a solid at room temperature and that is solublizable by the liquid fragrance, and wherein the fragrance-matrix mixture is in the form of a solid wafer when at 21° C.

7. The fragrance dispenser of claim 1 wherein the liquid fragrance makes up from 80 wt. % to 100 wt. % of the fragrance source.

8. The fragrance dispenser of claim 1 comprising:
   a base comprising a plurality of receptacles each with a major closed end and a major open end;
   a porous diffuser layer comprising sectional areas each of which occlusively overlies at least a portion of a major open end of a receptacle of the plurality of receptacles; and,
   a fragrance source provided within at least a portion of each receptacle and that comprises at least one volatilizable fragrance,
      wherein at least selected sectional areas of the porous diffuser layer are each individually removable from the porous diffuser layer to uncover at least a portion of a receptacle that the selected sectional area occlusively overlies.

9. The fragrance dispenser of claim 8 wherein the base comprises at least six receptacles and wherein the porous diffuser layer comprises at least six sectional areas that respectively occlusively overlie at least a portion of a major open end of each of the six receptacles, which six sectional areas are each frangibly connected to remaining areas of the porous diffuser layer so that the six sectional areas are each individually removable from the porous diffuser layer.

10. The fragrance dispenser of claim 8 wherein the major open end of each receptacle exhibits an area and wherein the sectional area of the porous diffuser layer that is individually removable from the porous diffuser layer, is configured so that removal of the sectional area of the porous diffuser layer uncovers from about 10% to about 100% of the area of the major open end of the receptacle that the sectional area of the porous diffuser layer occlusively overlies so as to allow accelerated emission of fragrance from that receptacle, while not allowing accelerated emission of fragrance from any other receptacle.

11. The fragrance dispenser of claim 8 wherein the major open end of each receptacle exhibits an area and wherein a sectional area of the porous diffuser layer that is individually removable from the porous diffuser layer, is configured so that removal of the sectional area of the porous diffuser layer uncovers from about 40% to about 60% of the area of the major open end of the receptacle that the sectional area of the porous diffuser layer occlusively overlies.

12. The fragrance dispenser of claim 8 wherein the individually removable sectional areas of the porous diffuser layer are frangibly connected to remaining areas of the porous diffuser layer by frangible connections that are provided by die cuts that extend through the entire thickness of the porous diffuser layer except at periodic bridging locations where the die cuts are interrupted to provide frangible bridges between the individually removable sectional areas of the porous diffuser layer and the remaining areas of the porous diffuser layer.

13. The fragrance dispenser of claim 12 wherein at least some of the periodic bridging locations are between adjacent edges of individually removable sectional areas of the porous diffuser layer.

14. The fragrance dispenser of claim 8 further comprising a removable cover sheet that overlies, and is removably adhesively bonded to, the porous diffuser layer; and, that comprises at least selected portions that are peelably detachable from the porous diffuser layer to expose the porous diffuser layer to initiate dispensing of the fragrance.

15. The fragrance dispenser of claim 14 wherein the dispenser comprises at least one indicia printed on a major surface of the base, of the porous diffuser layer, or of the removable cover sheet.

16. A method of dispensing fragrance into an atmosphere, the method comprising:
positioning a fragrance dispenser of claim 1 in the atmosphere;
if a removable cover sheet is present, removing at least a selected portion of the removable cover sheet from the fragrance dispenser;
and, removing at least one selected section of the porous diffuser layer to uncover an area of a major open end of a receptacle that the porous diffuser layer occlusively overlaid before being removed, to allow accelerated emission of fragrance from that receptacle.

17. The method of claim 16 wherein the method comprises sequential removal of selected sections of the porous diffuser layer, the sequential removals being spaced over a period of at least one day.

18. The method of claim 16 wherein the fragrance dispenser is positioned in a quiescent air environment in a location chosen from the group consisting of an interior of a room of a building and an interior of a vehicle.

19. The method of claim 16 wherein the fragrance dispenser is positioned in an airflow path in a location chosen from a group consisting of a position proximate an air filter of an HVAC system, a position proximate an air filter of a room air purifier, a position proximate an air filter of a vehicle, a position proximate a motorized fan, a position proximate an air vent of an HVAC system, and a position proximate an air vent of a vehicle climate-control system.

* * * * *